United States Patent
Allegretti et al.

(10) Patent No.: US 8,440,711 B2
(45) Date of Patent: May 14, 2013

(54) 2-ARYL-2-FLUOROPROPANOIC ACIDS AND DERIVATIVES AND PHARMACEUTICAL COMPOSITIONS CONTAINING THEM

(75) Inventors: Marcello Allegretti, L'Aquila (IT); Andrea Aramini, L'Aquila (IT); Maria Candida Cesta, L'Aquila (IT)

(73) Assignee: Dompe Pha.r.ma S.p.A., L'Aquila (IT)

( * ) Notice: Subject to any disclaimer, the term of this patent is extended or adjusted under 35 U.S.C. 154(b) by 298 days.

(21) Appl. No.: 12/519,567

(22) PCT Filed: Dec. 18, 2007

(86) PCT No.: PCT/IB2007/003994
§ 371 (c)(1),
(2), (4) Date: Oct. 16, 2009

(87) PCT Pub. No.: WO2008/075184
PCT Pub. Date: Jun. 26, 2008

(65) Prior Publication Data
US 2010/0076034 A1 Mar. 25, 2010

(30) Foreign Application Priority Data

Dec. 19, 2006 (EP) .................................... 06126496

(51) Int. Cl.
*A61K 31/02* (2006.01)
*C07C 63/04* (2006.01)
*C07C 233/02* (2006.01)
*C07D 207/30* (2006.01)
*C07D 209/04* (2006.01)

(52) U.S. Cl.
USPC ........... 514/415; 514/428; 514/461; 514/568; 514/617; 548/509; 548/561; 548/562; 549/82; 562/493; 564/161

(58) Field of Classification Search ... 562/493; 564/161, 564/182
See application file for complete search history.

(56) References Cited

FOREIGN PATENT DOCUMENTS

| EP | 0 276 122 | 7/1988 |
|---|---|---|
| WO | WO 2005/090295 | 9/2005 |

OTHER PUBLICATIONS

Goj, et al. Document No. 126:238154 (1997) retrieved from CAPLUS.*
Wang, et al. Journal of Molecular Catalysis B: Enzymatic 42 (2006) 90-94.*
Cancer and Metastasis Reviews (1998), 17(1), 91-106.*
Science (1999), vol. 286, 531-537.*
Melanoma [online] retrieved from the internet on Sep. 29, 2011, URL; http://www.ncbi.nlm.nih.gov/pubmedhealth/PMH0001853/.*
Crugnola, et al. (Document No. 109:170047, CAPLUS), 1988.*
Michel, et al. (Document No. 126:250785, CAPLUS), 1997.*
Takeuchi et al., "Biological Evaluation of 2-aryl-2-fluoropropionic Acids as Possible Platforms for New Medicinal Agents," Chemical Abstracts Service, Database accession No. 2005:1018111, Abstract, XP-002479149, Chemical & Pharmaceutical Bulletin, 53(8), pp. 1062-1064, 2005.
Goj et al., "Convenient Routes to 2-aryl-2-fluoropropionic Acids: Synthesis of Monofluorinated Analogs of (.+-.,)-ibuprofen,(.+-.)-naproxen and Related Compounds," Database accession No. 1996:596816, Abstract, XP-002479151, Tetrahedron, 52(39), pp. 12761-12774, 1996.
Michel et al., "No evidence for Intramolecular Hydrogen Bonds in .alpha.-fluoro Carboxamides," Database accession No. 1997:191723, Abstract, XP-002479150, Liebigs Annalen/Recueil, (3), pp. 517-519, 1997.
Schlosser, et al., ".alpha.-Fluoro Analogs of Inflammation Inhibiting .alpha.arylpropionic Acids," Database accession No. 1996:376452, Abstract, XP-002479152, Tetrahedron, 52(24), 8257-8262, 1996.
Amanetoullah et al., "Synthesis of 2-fluoro-acids, Esters, and Amides from .alpha.- dicyanoepoxides," Database accession No. 1996:136326, Abstract, Synthetic Communications, 26(6), pp. 1155-1161, 1996.
Barrelle et al., "Substituted 2-fluoroacetic Acids as Chiral Derivatizing Agents," Database accession No. 1995:718511, Abstract, XP-002479154, Journal Of Chemical Research, Synopses, (8), pp. 316-317, 1995.
De Menezes et al., "Inhibition of Prostaglandin F(2alpha) by Selective Cyclooxygenase 2 Inhibtors Accounts for Reduced rat Leukocyte Migration," Database accession No. 2006697491, Abstract, XP 002479482, Inflammation, vol. 29, No. 4-6, pp. 163-169, Dec. 2005.
Parnham, M.J., "Antirheumatic Agents and Leukocyte Recruitment: New Light on the Mechanism of action of Oxaceprol," Biochemical Pharmacology, vol. 58, pp. 209-215, 1999.

* cited by examiner

Primary Examiner — Shawquia Young
(74) Attorney, Agent, or Firm — King & Spalding

(57) ABSTRACT

The present invention relates to (R,S) 2-aryl-2-fluoropropanoic acids, their single enantiomers (R) and (S), their derivatives amides and acylsulfonamides and to pharmaceutical compositions containing them, which are used in the prevention and treatment of tissue damage due to the exacerbated recruitment of polymorphonucleated neutrophils (PMN leukocytes) at inflammation sites. The present invention provides compounds for use in the treatment of psoriasis, ulcerative colitis, melanoma, chronic obstructive pulmonary disease (COPD), bullous pemphigo, rheumatoid arthritis, idiopathic fibrosis, glomerulonephritis and in the treatment of damages caused by ischemia and reperfusion.

6 Claims, No Drawings

2-ARYL-2-FLUOROPROPANOIC ACIDS AND DERIVATIVES AND PHARMACEUTICAL COMPOSITIONS CONTAINING THEM

BRIEF DESCRIPTION OF THE INVENTION

The present invention relates to (R,S) 2-aryl-2-fluoropropanoic acids, their single enantiomers (R) and (S), their derivatives amides and acylsulfonamides and to pharmaceutical compositions containing them, which are used in the prevention and treatment of tissue damage due to the exacerbated recruitment of polymorphonucleated neutrophils (PMN leukocytes) at inflammation sites.

STATE OF THE ART

Particular blood cells (macrophages, granulocytes, neutrophils, polymorphonucleated) respond to a chemical stimulus (when stimulated by substances called chemokines) by migrating along the concentration gradient of the stimulating agent, through a process called chemotaxis. The main known stimulating agents or chemokines are represented by the breakdown products of complement C5a, some N-formyl peptides generated from lysis of the bacterial surface or peptides of synthetic origin, such as formyl-methionyl-leucyl-phenylalanine (f-MLP) and mainly by a variety of cytokines, including Interleukin-8 (CXCL8). Interleukin-8 is an endogenous chemotactic factor produced by most nucleated cells such as fibroblasts, macrophages.

In some pathological conditions, marked by exacerbated recruitment of neutrophils, a more severe tissue damage at the site is associated with the infiltration of neutrophilic cells. The role of neutrophilic activation in the determination of damage associated with post ischemia reperfusion and pulmonary hyperoxia has been widely demonstrated.

The biological activity of CXCL8 is mediated by the interaction of the chemokine with CXCR1 and CXCR2 membrane receptors which belong to the family of seven transmembrane receptors, expressed on the surface of human neutrophils and of certain types of T-cells (L. Xu et al., J. Leukocyte Biol., 57, 335, 1995). Selective ligands are known which can discriminate between CXCR1 and CXCR2: GROα is an example of a CXCR2 selective chemotactic factor.

Potential pathogenic role of CXCL8 in melanoma progression and metastasis could be mediated by CXCR2 activation [Varney M. L. et al., Am. J. Clin. Pathol., 125, 209, 2006].

The structures of the compounds object of the invention are related to the structures of the non fluorinated parent compounds already described as CXCL8, GRO-α and C5a inhibitors in WO 01/58852, WO 00/24710, WO 02/068377 and WO05/090295. It's known that the fluorine atom can be considered a bioisoster of hydrogen since it is a reasonable hydrogen mimic that exerts only a minor steric demand at receptor sites [O'Hagan et al., Chem. Commun., 7, 645, 1997]. In organic chemistry fluorine substitution can alter the chemical properties, disposition and biological activity of molecules or drugs. Although it is generally thought that fluorine for hydrogen causes minimal steric effects at receptor sites, the van der Waals radius of fluorine (1.47 Å) lies between that of oxygen (1.57 Å) and hydrogen (1.2 Å). More, hydrogen and fluorine have quite different electronic properties; fluorine is the most electronegative element in the periodic table and the replacement of a hydrogen for fluorine can alter the pKa value, the chemical reactivity and the stability of a molecule and, inside a molecule, of the neighbouring functional groups. The isosteric replacement of the hydrogen by fluorine is also a strategy used in medicinal chemistry to improve the metabolic stability by blocking metabolically labile sites. However, this kind of strategy usually leads to a modification of the biological activity. For example, the introduction of a fluorine into the α position of 2-arylpropanoic acids causes a dramatic loss of anti-inflammatory activity [Takeuchi Y. et al., Chem. Pharm. Bull., 53, 1062, 2005].

We have now found out that a novel class of 2-aryl-2-fluoropropanoic acids and derivatives (amides and N-acylsulfonamides) shows the ability to effectively inhibit CXCL8 and C5a induced neutrophils chemotaxis and degranulation.

DETAILED DESCRIPTION OF THE INVENTION

The introduction of a fluorine atom into the α position of "profens" does not allow any inversion, chemical or enzymatic, of the configuration at the asymmetric centre. The term "profen" indicates a molecule belonging to the 2-arylpropanoic acids family. We have now found that the substitution at the stereogenic center of hydrogen by fluorine of the compounds of the present invention, not only prevents the possibility of racemization, but improves both the pharmacokinetics and the metabolism of these compounds. In fact, the increase of pharmacokinetics parameters as $t_{1/2}$ and Vd and the lack of formation of unwanted metabolites are observed for the compounds belonging to the novel class.

The present invention thus provides (R,S)-2-aryl-2-fluoropropanoic acids and derivatives of formula (I) and their single (R) and (S) enantiomers,

(I)

and pharmaceutically acceptable salts thereof,
wherein
Ar is a phenyl group unsubstituted or substituted by one or more groups independently selected from halogen, C1-C4-alkyl, C2-C4-alkenyl, C2-C4-alkynyl, C1-C4-alkoxy, hydroxy, C1-C4-acyloxy, phenoxy, cyano, nitro, amino, C1-C4-acylamino, halo-C1-C3-alkyl, halo-C1-C3-alkoxy, benzoyl, heteroarylcarbonyl, heteroaryl, linear or branched C1-C8-alkanesulfonate, linear or branched C1-C8-alkanesulfonamides, linear or branched C1-C8 alkyl sulfonylmethyl;
or Ar is a heteroaryl ring selected from pyridine, pyrrole, tiofene, furane, indole;
R is OH or a residue of formula NR'R"
wherein
R' group is selected from
H, OH and
when R' is H, R" is selected from
H, $C_1$-$C_5$-alkyl, $C_3$-$C_6$-cycloalkyl, $C_2$-$C_5$-alkenyl, $C_1$-$C_5$-alkoxy;
an heteroaryl group selected from substituted and unsubstituted pyridine, pyrimidine, pyrrole, thiofene, furane, indole, thiazole, oxazole;
an amino acid residue consisting of straight or branched $C_1$-$C_6$-alkyl, $C_3$-$C_6$-cycloalkyl, $C_2$-$C_6$-alkenyl, $C_1$-$C_6$-phenylalkyl, substituted with one further carboxy (COON) group;
a residue of formula —$CH_2$—$CH_2$—Z—($CH_2$—$CH_2$O)nR' wherein R' is H or $C_1$-$C_5$-alkyl, n is an integer from 0 to 2 and Z is oxygen or sulfur;

a residue of formula —(CH$_2$)n-NRaRb wherein n is an integer from 0 to 5 and each Ra and Rb, which may be the same or different, are C$_1$-C$_6$-alkyl, C$_2$-C$_6$-alkenyl or, alternatively, Ra and Rb, together with the nitrogen atom to which they are bound, form a heterocycle from 3 to 7 members of formula (II).

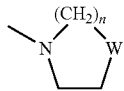
(II)

wherein W represents a single bond, O, S, N-Rc, Rc being H, C$_1$-C$_6$-alkyl or C$_1$-C$_6$-alkylphenyl, and n is an integer from 0 to 3, a residue of formula SO$_2$Rd wherein Rd is C$_1$-C$_6$-alkyl, C$_3$-C$_6$-cycloalkyl, C$_2$-C$_6$-alkenyl, aryl and heteroaryl;

when R' is OH, R" is selected from

H, C$_1$-C$_5$-alkyl, C$_3$-C$_6$-cycloalkyl, C$_2$-C$_5$-alkenyl;

with the proviso that compounds of the general formula (I) exclude 2-(3-benzoylphenyl)-2-fluoropropanoic acid.

Preferred compounds according to the invention are those wherein:

Ar is a phenyl group unsubstituted or substituted by one or more groups independently selected from: C1-C4-alkyl, benzoyl, 4-trifluoromethyl-2-amino-thiazole, 4-trifluoromethyl-2-amino-oxazole, trifluoromethanesulfonyloxy, trifluoromethanesulfonylamino, benzylsulfonyloxy, benzenesulfonyloxy, 2'-chlorobenzenesulfonyloxy, methanesulfonylamino, 2-propanesulfonylamino, benzylsulfonylamino, benzenesulfonylamino, 2'-ethylbenzenesulfonylamino, aminosulfonylmethyl, 2'-chlorobenzenesulfonylamino, benzenesulfonylmethyl, aminosulfonyloxy, aminosulfonylamino;

R is OH or a residue of formula NR'R"
wherein
when R' is H, R" is selected from
H, C$_1$-C$_5$ alkyl, C$_3$-C$_6$ cycloalkyl, C$_1$-C$_6$ alkoxy, C$_1$-C2-carboxyalkyl;
an heteroaryl group selected from substituted and unsubstituted pyridine, thiazole, oxazole;
a residue of formula —(CH$_2$)n-NRaRb wherein n is the integer 2 or 3, more preferably 3 and the group NRaRb is N,N-dimethylamine, N,N-diethylamine, 1-piperidyl, 1-pirrolidinyl, 4-morpholyl, 1-pyrrolidyl, 1-piperazinyl, 1-(4-methyl)piperazinyl;
a residue of formula SO$_2$Rd wherein Rd is C$_1$-C$_2$-alkyl, C$_3$-C$_6$ cycloalkyl.
when R' is OH, R" is
H, C$_1$-C$_5$ alkyl, C$_3$-C$_6$ cycloalkyl.

Particularly preferred compounds of the invention are:
2-fluoro-2-(4-{[(trifluoromethyl)sulfonyl]oxy}phenyl) propanoic acid;
(2S)-2-fluoro-2-(4-{[(trifluoromethyl)sulfonyl]oxy}phenyl) propanoic acid;
(2R)-2-fluoro-2-(4-{[(trifluoromethyl)sulfonyl]oxy}phenyl) propanoic acid;
4-[(1S)-1-fluoro-2-(hydroxyamino)-1-methyl-2-oxoethyl}phenyl trifluoromethanesulfonate;
4-[(1S)-1-fluoro-2-[hydroxyl(methyl)amino]-1-methyl-2-oxoethyl}phenyl trifluoromethanesulfonate;
2-(3-benzoylphenyl)-2-fluoropropanoic acid;
2-fluoro-2-(3-{[4-(trifluoromethyl)-1,3-thiazol-2-yl]amino}phenyl)propanoic acid;
4-(2-amino-1-fluoro-1-methyl-2-oxoethyl)phenyl trifluoromethanesulfonate;
4-[(1R)-2-amino-1-fluoro-1-methyl-2-oxoethyl)phenyl trifluoromethanesulfonate;
4-[(1S)-2-amino-1-fluoro-1-methyl-2-oxoethyl)phenyl trifluoromethanesulfonate;
4-[1-fluoro-2-(methoxyamino)-1-methyl-2-oxoethyl]phenyl trifluoromethanesulfonate;
4-[1-fluoro-2-(isopropylamino)-1-methyl-2-oxoethyl]phenyl trifluoromethanesulfonate;
2-(3-benzoylphenyl)-2-fluoropropanamide;
2-fluoro-2-(3-{([4-(trifluoromethyl)-1,3-thiazol-2-yl]amino}phenyl)propanamide;
(2S)-2-{[(2R)-2-fluoro-2-(3-{[4-(trifluoromethyl)-1,3-thiazol-2-yl]amino}phenyl)propanoyl]amino}propanoic acid;
(2S)-2-{[2-fluoro-2-(3-{[4-(trifluoromethyl)-1,3-thiazol-2-yl]amino}phenyl)propanoyl]amino}propanoic acid;
4-{(1R)-1-fluoro-1-methyl-2-[(methylsulfonyl)amino]-2-oxoethyl}phenyl trifluoromethanesulfonate;
4-{(1S)-1-fluoro-1-methyl-2-oxo-2-(2-pyrrolidin-1-ylethyl) amino]ethyl}phenyl trifluoromethanesulfonate;
4-((1R)-1-fluoro-1-methyl-2-oxo-2-{[(2R)-pyrrolidin-2-ylmethyl]amino}ethyl)phenyl trifluoromethanesulfonate.

The present invention further provides compounds of formula (I) for use as medicaments. In particular, such medicaments are inhibitors of the chemotaxis of polymorphonucleate and mononucleate cells.

Structures of compounds of formula (I) are related to the structures of the non fluorinated parent compounds already described as CXCL8, GRO-α and C5a inhibitors in WO 01/58852, WO 00/24710, WO 02/068377 and WO05/090295, but they show significant advantageous characteristics as compared to the preferred compounds of the above cited inventions.

The molecules of the invention show that, surprisingly, the introduction of a fluorine into the α position of the "profen", not only retains the desired biological activity, but improves the pharmacokinetic profile and allows to dissociate the biological activity from the unwanted effects due to the accumulation and consequent slow elimination of the specific metabolite.

As reported above, the introduction of the fluorine atom in the α position of the 2-aryl-2-fluoropropanoic acids leads to a dramatic decrease of anti-inflammatory activity linked to COX inhibition in comparison with corresponding NSAIDs not fluorinated, affecting the balance of COX-1 and COX-2. Both the R and the S enantiomers of 2-aryl-2-fluoropropanoic acids and derivatives here described are inactive in the inhibition of cyclooxygenases.

Surprisingly, molecules object of the invention preserve the ability to effectively inhibit CXCL8, GRO-α and C5a induced neutrophils chemotaxis and degranulation as the corresponding non fluorinated compounds (Tables 1 and 2).

The fluorine substitution improves in terms of pharmacokinetic profile (longer half-life time t½ and Vd increase, Table 3).

Furthermore, the introduction of a fluorine into the α position of 2-arylpropanoic acids does not allow the formation of the unwanted α-hydroxylated metabolite.

The effect of the substitution on the in vivo behaviour of the molecules is not predictable and it relies with the position of the substituents and with the new pattern of interactions established by the fluorinated molecule with the molecular target.

These characteristics confer to the novel molecules an optimal overall pharmacological profile and allow the therapeutic use in several chronic or acute pathological conditions.

The compounds of the invention of formula (I) are generally isolated or in neutral form or in the form of their addition salts with both organic and inorganic pharmaceutically acceptable acids or bases.

Examples of such acids are selected from hydrochloric acid, sulfuric acid, phosphoric acid, metansulfonic acid, fumaric acid, citric acid.

Examples of such bases are sodium hydroxide, potassium hydroxide, calcium hydroxide, (D,L)-Lysine, L-Lysine, tromethamine.

The compounds of the invention of formula (I) were evaluated in vitro for their ability to inhibit chemotaxis of polymorphonucleate leukocytes (hereinafter referred to as PMNs) and monocytes induced by the fractions of CXCL8 and GRO-α and C5a and compared to the corresponding non fluorinated parent compounds. For this purpose, in order to isolate the PMNs from heparinized human blood, taken from healthy adult volunteers, mononucleates were removed by means of sedimentation on dextran (according to the procedure disclosed by W. J. Ming et al., J. Immunol., 138, 1469, 1987) and red blood cells by a hypotonic solution. The cell vitality was calculated by exclusion with Trypan blue, whilst the ratio of the circulating polymorphonucleates was estimated on the cytocentrifugate after staining with Diff Quick.

In the CXCL8 induced chemotaxis assay human recombinant CXCL8 (Pepro Tech) was used as stimulating agents in the chemotaxis experiments: the lyophilized protein was dissolved in a volume of HBSS containing 0.2% bovin serum albumin (BSA) so thus to obtain a stock solution having a concentration of $10^{-5}$ M to be diluted in HBSS to a concentration of $10^{-9}$ M, for the chemotaxis assays.

GRO-α induced chemotaxis inhibition was evaluated in an analogous assay.

In the C5a induced chemotaxis assay the fractions hr-C5a and hrC5a-desArg (Sigma) were used as stimulating agents in chemotaxis experiments, obtaining practically identical results. Lyophilized C5a was dissolved in a volume of HBSS containing 0.2% BSA so as to obtain a stock solution having a concentration of $10^{-5}$ M, to be diluted in HBSS to a concentration of $10^{-9}$ M, for the chemotaxis assays.

In the chemotaxis experiments, the PMNs were incubated with the compounds of the invention of formula (I) for 15' at 37° C. in an atmosphere containing 5% $CO_2$.

The chemotactic activity of the C5a was evaluated on human circulating polymorphonucleates (PMNs) resuspended in HBSS at a concentration of $1.5 \times 10^6$ PMNs per nil.

During the chemotaxis assay (W. Falket et al., J. Immunol. Methods, 33, 239, 1980) PVP-free filters with a porosity of 5 μm and microchambers suitable for replication were used.

The compounds of the invention in formula (I) were evaluated at a concentration ranging between $10^{-6}$ and $10^{-10}$ M; for this purpose they were added, at the same concentration, both to the lower pores and the upper pores of the microchamber. Evaluation of the ability of the compounds of the invention of formula (I) to inhibit the chemotaxis of human monocytes was carried out according to the method disclosed (Van Damme J. et al., Eur. J. Immunol., 19, 2367, 1989).

Protein Binding was determined as follows: Duplicate rat plasma samples of each compound at 50 μg/mL concentration were incubated at 37° C. for 20 minutes under gentle shaking. Then samples were ultrafiltrated through Centrifree® micropartition devices by centrifugation at 1500 g for 15 minutes. The ultrafiltrate was subjected to HPLC-MS/MS quantitative analysis (Column Luna C18, 150×2 mm ID 5 μm (Phenomenex), mobile phase: eluent A) 0.02M HCOO—$NH_4$+ (pH 4.3 with HCOOH); eluent B) $CH_3OH$).

The pharmacokinetic profile of the compounds of formula (I) was evaluated in male mice or rats after intravenous and oral administration. The pharmacokinetic analysis was performed using plasmatic concentrations of the compounds at different times. The data were evaluated by Kinetica 2000™, Version 3.0 Software [InnaPhase Corporation, World headquarters, 1700 Race Street, Philadelphia, Pa. 19103 USA]. The pharmacokinetic parameters were calculated according to the following formulas:

Kel=elimination rate constant;

$t_{1/2}$=In2/Kel, $AUC=AUC_0n+AUC$extra, where $AUC_0$n=AUC from t=0 to t last (Trapezoidal Method) and AUCextra=extrapolated AUC=Clast/Kel;

Clearance=D/AUC;

Vd=Cl/Kel;

Oral bioavailability $F=(AUC_{p.o.}/AUC_{i.v.})*(D_{i.v.}/D_{p.o.})*100$.

The compounds of formula (I), evaluated ex vivo in the blood in toto according to the procedure disclosed by Patrignani et al., in J. Pharmacol. Exper. Ther., 271, 1705, 1994, were found to be totally ineffective as inhibitors of cyclooxygenase (COX) enzymes.

In most cases, the compounds of formula (I) do not interfere with the production of $PGE_2$ induced in murine macrophages by lipopolysaccharides stimulation (LPS, 1 μg/mL) at a concentration ranging between $10^{-5}$ and $10^{-7}$ M. Inhibition of the production of $PGE_2$ which may be recorded, is mostly at the limit of statistical significance, and more often is below 15-20% of the basal value.

The reduced effectiveness in the inhibition of the COXs constitutes an advantage for the therapeutical application of compounds of the invention in as much as the inhibition of prostaglandin synthesis constitutes a stimulus for the macrophage cells to amplify synthesis of TNF-α (induced by LPS or hydrogen peroxide) that is an important mediator of the neutrophilic activation and stimulus for the production of the CXCL8.

In view of the experimental evidence discussed above and of the role performed by CXCL8 and by the complement cascade, and namely its fraction C5a, in the processes involving the activation and the infiltration of neutrophils, the compounds of the invention are particularly useful in the treatment of diseases such as psoriasis (Nicholoff R. J. et al., Am. J. Pathol., 138, 129, 1991), intestinal chronic inflammatory pathologies such as ulcerative colitis (Mahida Y. R. et al., Clin. Sci., 82, 273, 1992), melanoma, chronic obstructive pulmonary disease (COPD), bullous pemphigoid, rheumatoid arthritis (Selz M. et al., J. Clin. Invest., 87, 463, 1981), idiopathic fibrosis (Miller E. J., previously cited and Carré P. C. et al., J. Clin. Invest., 88, 1882, 1991), glomerulonephritis (Wada T. et al., J. Exp. Med., 180, 1135, 1994) and in the prevention and treatment of damages caused by ischemia and reperfusion.

It is therefore a further object of the present invention to provide compounds for use in the treatment of psoriasis, ulcerative colitis, melanoma, chronic obstructive pulmonary disease (COPD), bullous pemphigo, rheumatoid arthritis, idiopathic fibrosis, glomerulonephritis and in the treatment of damages caused by ischemia and reperfusion.

TABLE 1

Biological activity of the preferred compounds

| Name | Structure | CXCL8 (% inhibition at $10^{-9}$ M) | GRO-α (% inhibition at $10^{-8}$ M) |
|---|---|---|---|
| 2-fluoro-2-(4-{[(trifluoromethyl)sulfonyl]oxy}phenyl)propanoic acid (1) | 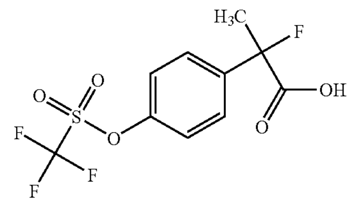 [SMILES: CC(F)(C(=O)O)c1ccc(OS(=O)(=O)C(F)(F)F)cc1] | n.a. | 47 ± 10* |
| (2S)-2-fluoro-2-(4-{[(trifluoromethyl)sulfonyl]oxy}phenyl)propanoic acid (2) | 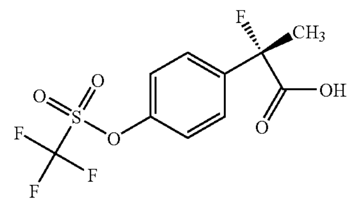 [SMILES: C[C@@](F)(C(=O)O)c1ccc(OS(=O)(=O)C(F)(F)F)cc1] | n.a. | 43 ± 15* |
| (2R)-2-fluoro-2-(4-{[(trifluoromethyl)sulfonyl]oxy}phenyl)propanoic acid (3) | 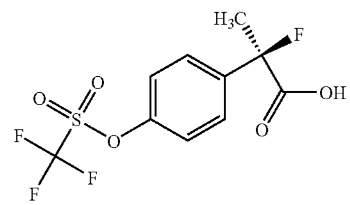 [SMILES: C[C@](F)(C(=O)O)c1ccc(OS(=O)(=O)C(F)(F)F)cc1] | n.a. | 49 ± 6* |
| 4-[(1S)-1-fluoro-2-(hydroxyamino)-1-methyl-2-oxoethyl}phenyl trifluoromethanesulfonate (4) | 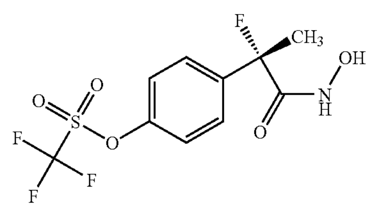 [SMILES: C[C@@](F)(C(=O)NO)c1ccc(OS(=O)(=O)C(F)(F)F)cc1] | n.a. | 55 ± 10 |
| 4-[(1S)-1-fluoro-2-[hydroxyl(methyl)amino]-1-methyl-2-oxoethyl}phenyl trifluoromethanesulfonate (5) | 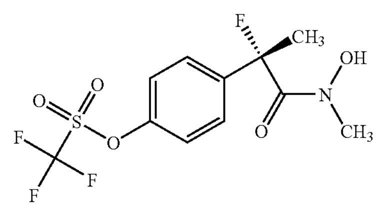 [SMILES: CN(O)C(=O)[C@@](C)(F)c1ccc(OS(=O)(=O)C(F)(F)F)cc1] | n.a. | 40 ± 8 |
| 2-(3-benzoylphenyl)-2-fluoropropanoic acid (6) | 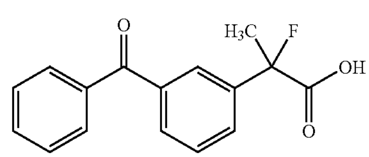 [SMILES: CC(F)(C(=O)O)c1cccc(C(=O)c2ccccc2)c1] | n.a. | 42 ± 4 |
| 2-fluoro-2-(3-{[4-(trifluoromethyl)-1,3-thiazol-2-yl]amino}phenyl)propanoic acid (7)** | 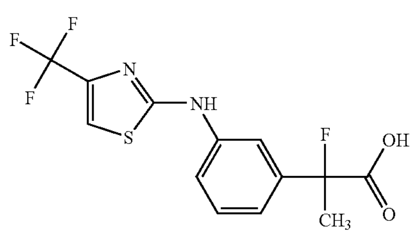 [SMILES: CC(F)(C(=O)O)c1cccc(Nc2nc(C(F)(F)F)cs2)c1] | 21 ± 6 | 60 ± 10 |

TABLE 1-continued

Biological activity of the preferred compounds

| Name | Structure | CXCL8 (% inhibition at $10^{-9}$ M) | GRO-α (% inhibition at $10^{-8}$ M) |
|---|---|---|---|
| 4-(2-amino-1-fluoro-1-methyl-2-oxoethyl)phenyl trifluoromethanesulfonate (8) | 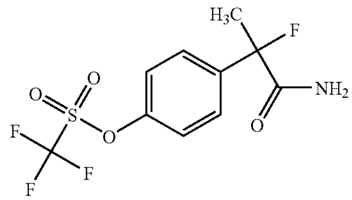 [SMILES: CC(F)(C(N)=O)c1ccc(OS(=O)(=O)C(F)(F)F)cc1] | 50 ± 9 | 57 ± 12 |
| 4-[(1R)-2-amino-1-fluoro-1-methyl-2-oxoethyl)phenyl trifluoromethanesulfonate (9) | 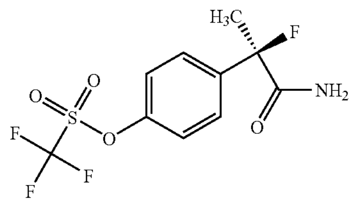 [SMILES: C[C@](F)(C(N)=O)c1ccc(OS(=O)(=O)C(F)(F)F)cc1] | n.a. | 53 ± 9 |
| 4-[(1S)-2-amino-1-fluoro-1-methyl-2-oxoethyl)phenyl trifluoromethanesulfonate (10) | 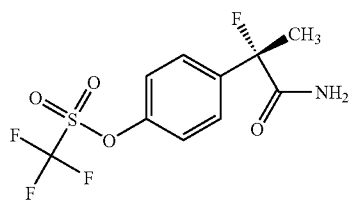 [SMILES: C[C@@](F)(C(N)=O)c1ccc(OS(=O)(=O)C(F)(F)F)cc1] | 50 ± 6 | 10 ± 12 |
| 4-[1-fluoro-2-(methoxyamino)-1-methyl-2-oxoethyl]phenyl trifluoromethanesulfonate (11) | 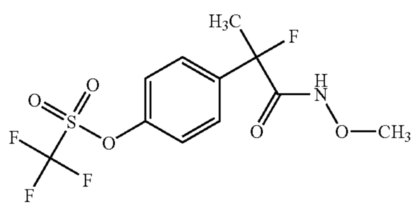 [SMILES: CONC(=O)C(C)(F)c1ccc(OS(=O)(=O)C(F)(F)F)cc1] | 40 ± 10* | 7 ± 8 |
| 4-[1-fluoro-2-(isopropylamino)-1-methyl-2-oxoethyl]phenyl trifluoromethanesulfonate (12)** | 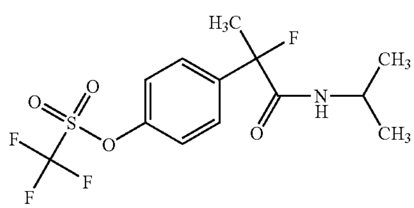 | n.a. | 45 ± 8* |
| (2S)-2-{[(2R)-2-fluoro-2-(4-{[(trifluoromethyl)sulfonyl]oxy}phenyl)propanoyl]amino}propanoic acid (15) | 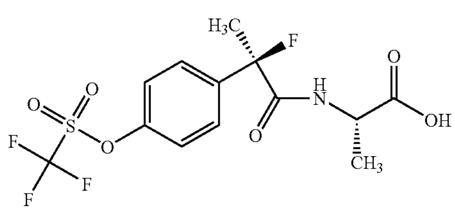 [SMILES: C[C@H](NC(=O)[C@](C)(F)c1ccc(OS(=O)(=O)C(F)(F)F)cc1)C(=O)O] | 55 ± 8 | n.a. |
| (2S)-2-{[2-fluoro-2-(3-{[4-(trifluoromethyl)-1,3-thiazol-2-yl]amino}phenyl)propanoyl]amino}propanoic acid (16) | 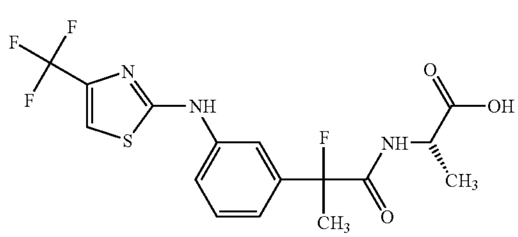 | 50 ± 12 | n.a. |

TABLE 1-continued

Biological activity of the preferred compounds

| Name | Structure | CXCL8 (% inhibition at $10^{-9}$ M) | GRO-α (% inhibition at $10^{-8}$ M) |
|---|---|---|---|
| 4-{(1R)-1-fluoro-1-methyl-2-[(methylsulfonyl)amino]-2-oxoethyl}phenyl trifluoromethanesulfonate (17) | 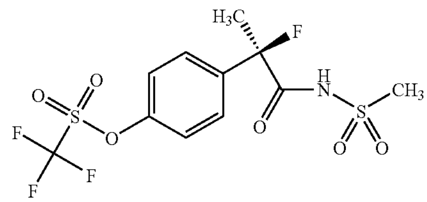 [SMILES: C[C@](F)(C(=O)NS(C)(=O)=O)c1ccc(OS(=O)(=O)C(F)(F)F)cc1] | n.a. | 57 ± 14 |

(*) % of inhibition at $10^{-7}$ M

TABLE 2

Biological activity of the preferred compounds

| Name | Structure | CSCL8 (% inhibition at $10^{-9}$ M) | GRO-α (% inhibition at $10^{-8}$ M) | C5a (% inhibition at $10^{-8}$ M) |
|---|---|---|---|---|
| 2-(3-benzoylphenyl)-2-fluoropropanamide (13) | 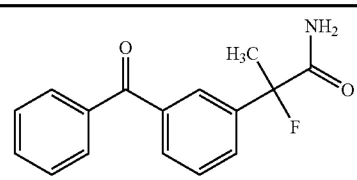 | 52 ± 8* | 50 ± 12* | 47 ± 9 |
| 2-fluoro-2-(3-{[4-(trifluoromethyl)-1,3-thiazol-2-yl]amino}phenyl)propanamide (14) | 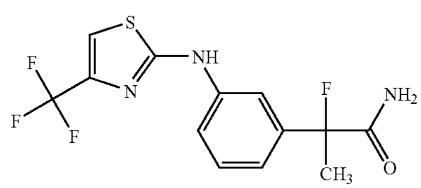 [SMILES: CC(F)(C(N)=O)c1cccc(Nc2nc(C(F)(F)F)cs2)c1] | 36 ± 12 | 55 ± 7 | 33 ± 5 |
| 4-{(1S)-1-fluoro-1-methyl-2-oxo-2-(2-pyrrolidin-1-ylethyl)amino]ethyl}phenyl trifluoromethanesulfonate (18) | 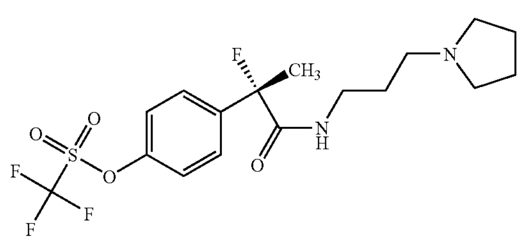 [SMILES: C[C@@](F)(C(=O)NCCCN1CCCC1)c1ccc(OS(=O)(=O)C(F)(F)F)cc1] | n.a. | n.a. | 53 ± 5 |
| 4-((1R)-1-fluoro-1-methyl-2-oxo-2-{[(2R)-pyrrolidin-2-ylmethyl]amino}ethyl)phenyl trifluoromethanesulfonate (19) | 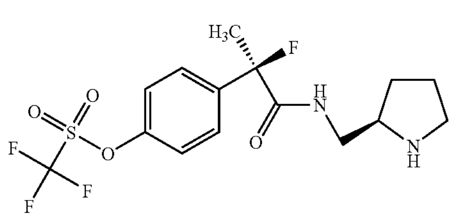 [SMILES: C[C@](F)(C(=O)NC[C@H]1CCCN1)c1ccc(OS(=O)(=O)C(F)(F)F)cc1] | n.a. | n.a. | 45 ± 4 |

TABLE 3

Pharmacokinetic data of exemplary compounds of formula (I)
in comparison with parent compounds and with the metabolite (B) derived
from (A). Experiments were performed in rat.

| Compound | Protein Binding | $t_{1/2}$ (h) | Oral bioavailability (%) | Vd (mL/kg) | Clearance (mL/h/kg) |
|---|---|---|---|---|---|
| 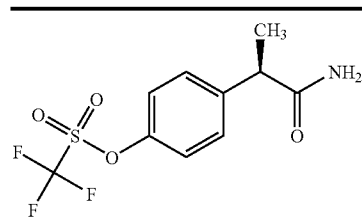 (A) WO 05/090295 | 94% | 1.9 | 72 | 550 | 220 |
| 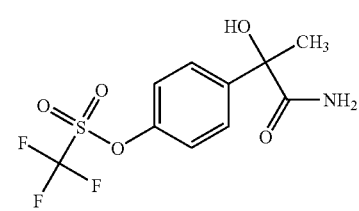 (B) | 80% | 25 | 85 | 1330 | 39 |
| 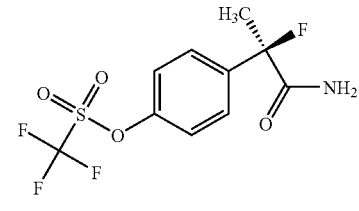 | 95%* | 13.8 | 46.8 | 631 | 31.8 |
| 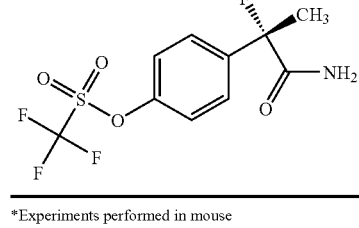 | 92%* | 9.1 | 84.2 | 1470 | 137 |

*Experiments performed in mouse

Pharmaceutical compositions comprising a compound of the invention and a suitable carrier thereof, are also within the scope of the present invention.

The compounds of the invention, together with a conventionally employed adjuvant, carrier, diluent or excipient may, in fact, be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the compounds of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined on the basis of relevant circumstances including the condition to be treated, the chosen route of administration, the actual compound administered, the age, weight, and response of the individual patient, the severity of the patient's symptoms, and the like.

The pharmaceutical compositions of the invention can be administered by a variety of routes including oral, rectal, transdermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non aqueous vehicle with buffers, suspending and dispensing agents, colorants, flavours and the like. Liquid forms, including the injectable compositions described here below, are always stored in the absence of light, so as to avoid any catalytic effect of light, such as hydroperoxide or peroxide formation. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavouring agent such as peppermint, methyl salicylate, or orange flavouring.

Injectable compositions are typically based upon injectable sterile saline or phosphate-buffered saline or other injectable carriers known in the art. As above mentioned, the acid derivative of formula (I) in such compositions is typically a minor component, frequently ranging between 0.05 to 10% by weight with the remainder being the injectable carrier and the like. The mean daily dosage will depend upon various factors, such as the seriousness of the disease and the conditions of the patient (age, sex and weight). The dose will generally vary from 1 mg or a few mg up to 1500 mg of the compounds of formula (I) per day, optionally divided into multiple administrations. Higher dosages may be administered also thanks to the low toxicity of the compounds of the invention over long periods of time.

The above described components for orally administered or injectable compositions are merely representative. Further materials as well as processing techniques and the like are set out in Part 8 of "Remington's Pharmaceutical Sciences Handbook", 18$^{th}$ Edition, 1990, Mack Publishing Company, Easton, Pa., which is incorporated herein by reference.

The compounds of the invention can also be administered in sustained release forms or from sustained release drug delivery systems. A description of representative sustained release materials can also be found in the incorporated materials in the Remington's Handbook as above.

The present invention shall be illustrated by means of the following examples which are not construed to be viewed as limiting the scope of the invention.

A further object of the invention is the process of preparation of compounds of formula (I).

The preparation of the compounds of formula (I) wherein R is a group as defined above, but is not OH, has been carried out using known methods such as the reaction of an activated form of an 2-arylpropionic acid of formula (II), or its (R) or (S) enantiomers,

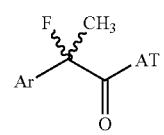

(III)

wherein:

AT is the residue activating the carboxy group. Examples of activated forms of 2-arylpropionic acids are chlorides (AT=Cl), imidazolides (AT=1-imidazole), phenol esters such as p-nitrophenol (AT=p-NO2-C6H4O—) or activated forms obtained by reaction in the presence of 1-hydroxybenzotriazole (HOBZ) or of a carbodiimide, for example dicyclohexylcarbodiimide, with an amine of formula NHR'R", wherein R' and R" are as defined above, in non-racemizing conditions, preferably in the presence of a molar excess of a base.

For Example, the fluorinated acid 1 was synthesized according known procedures starting from commercial 4-hydroxy-mandelic acid. The fluorination of the intermediate 2-[4-(trifluoromethanesulfonyloxy)phenyl]-2-hydroxy propanamide was performed using (diethylamino)sulfur trifluoride (DAST). The two enantiomers were obtained by optical resolution of the racemate using the chiral base cinchonidine. The S enantiomer was isolated after precipitation from the reaction mixture, while the R enantiomer was recovered by the mother liquors. Both the enantiomers were obtained with high optical purity (>95%). The most preferred compounds of the invention, 9 and 10, were synthesized starting from S and R acids, 2 and 3, by reaction of the corresponding acid chlorides with gaseous ammonia.

The following examples illustrate the invention.

Example 1

2-Fluoro-2-(4-{[(trifluoromethyl)sulfonyl]oxy}phenyl) propanoic acid (1)

To a solution of commercial 4-hydroxy-mandelic acid (10.0 gr, 0.05 mol) in acetone (160 ml), 2,2-dimethoxypropane (56 mL, 0.45 mol) and BF$_3$.Et$_2$O (0.4 ml, 0.48 mol)) were added under vigorous stirring. The solution was left stirring for 3 hours. After adding of triethylamine (TEA) (2 mL), the solvent was evaporated under vacuum and the crude diluted in a saturated solution of Na$_2$HCO$_3$ (30 ml) and extracted with EtOAc (3×30 ml). The collected organic extracts were washed with brine (2×25 mL), dried over Na$_2$SO$_4$ and evaporated under vacuum to give the intermediate 5-(4-hydroxyphenyl)-2,2-dimethyl-1,3-dioxolan-4-one (10.21 g) as yellow oil, pure enough to be used in the further step without any purification.

To a cooled solution (T=0° C.) of the 5-(4-hydroxyphenyl)-2,2-dimethyl-1,3-dioxolan-4-one (10.2 g) in dry CH$_2$Cl$_2$ (150 ml), TEA (20 ml) was added under vigorous stirring. The mixture was cooled at T=−20° C. and trifluoromethanesulfonic anhydride (10 ml) was added by dripping in 30 minutes. At the end of the addings the ice bath was removed and the reaction mixture stirred overnight at room temperature.

The reaction mixture was trasferred into a separator funnel and the organic layer washed with a buffer solution (pH 4.2) (3×100 ml) and with brine (2×70 mL), dried over Na$_2$SO$_4$ and evaporated under vacuum to give 4-(2,2-dimethyl-5-oxo-1,3-dioxolan-4-yl)phenyl trifluoromethanesulfonate (15.9 g) as brown oil pure enough to be used in the further step without any purification.

To a cooled solution (T=−78° C.) of lithium hexamethyldisilazane (47 mL, 1M in n-Hexane) a solution of 4-(2,2-dimethyl-5-oxo-1,3-dioxolan-4-yl)phenyl trifluoromethanesulfonate (15.9 g) in dry THF (100 ml) was added dropwise under vigorous stirring in 30 minutes. The resulting mixture was left stirring for 1 hour at T=−78° C.; $CH_3I$ (3.42 mL, 0.055 mol) was added. The ice bath was removed and the solution was left under stirring overnight at room temperature.

After addition of a buffer solution (pH 2.0, 100 ml), the reaction mixture was trasferred into a separator funnel and extracted with $Et_2O$ (3×100 mL). The organic collected extracts were washed with brine (2×70 mL), dried over $Na_2SO_4$ and evaporated under vacuum to give 4-(2,2,4-trimethyl-5-oxo-1,3-dioxolan-4-yl)phenyl trifluoromethanesulfonate (15.6 g) as a brown oil pure enough to be used in the further step without any purification.

A solution of 4-(2,2,4-trimethyl-5-oxo-1,3-dioxolan-4-yl) phenyl trifluoromethanesulfonate (15.5 g, 0.044 mol) in ammonia solution (30 mL, 7N in methanol) was left under stirring overnight at room temperature. After solvent evaporation under vacuum a crude was obtained that, after purification by flash chromatography ($CH_2Cl_2$/MeOH 98:2) afforded pure 2-[4-(trifluoromethanesulfonyloxy)phenyl]-2-hydroxy propanamide (9.7 g, 0.031 mol) as a white solid. Yield 70%. mp 105-107° C. $^1$H-NMR ($CDCl_3$) δ 7.80 (d, 2H, J=7 Hz), 7.35 (d, 2H, J=7 Hz), 6.50 (bs, 1H, CONH), 5.42 (bs, 1H, CONH), 3.05 (bs, 1H, OH), 1.94 (s, 3H).

To a cooled solution (T=−60° C.) of 2-[4-(trifluoromethanesulfonyloxy)phenyl]-2-hydroxy propanamide (6 g, 0.019 mol) in dry $CH_2Cl_2$ (60 mL), (diethylamino)sulfur trifluoride (3 mL, 0.023 mol) was added under vigorous stirring. The resulting mixture was left stirring overnight at room temperature. After addition of a buffer solution (pH 5.0, 100 mL), the reaction mixture was transferred into a separatory funnel and extracted with $CH_2Cl_2$ (3×100 mL). The collected organic extracts were washed with water (100 mL), dried over $Na_2SO_4$ and evaporated under vacuum to give a crude that, after pulping in n-hexane, afforded pure (R,S)-2-[4-(trifluoromethanesulfonyloxy)phenyl]-2-fluoro-propanamide (5.31 g, 0.017 mol) as brown solid. Yield 89%. mp 85-87° C. $^1$H-NMR ($CDCl_3$) δ 7.75 (d, 2H, J=7 Hz), 7.30 (d, 2H, J=7 Hz), 6.42 (bs, 1H, CONH), 5.47 (bs, 1H, CONH), 1.95 (d, 3H, J=23 Hz).

To a solution of (R,S)-2-[4-(trifluoromethanesulfonyloxy) phenyl]-2-fluoro-propanamide (5.3 g, 0.017 mol) in 1,4-dioxane (35 mL), conc. HCl (2 mL) was added under vigorous stirring and the solution was left at reflux for 48 h. After solvent evaporation under vacuum the crude was diluted in water (30 mL) and extracted with EtOAc (3×30 mL). The collected organic extracts were washed with brine (2×25 mL), dried over $Na_2SO_4$ and evaporated under vacuum to give the pure (R,S)-2-[4-(trifluoromethanesulfonyloxy)phenyl]-2-fluoro-propanoic acid 1 (0.015 mol) as white solid. Yield 90%. mp 124-125° C. $^1$H-NMR ($CDCl_3$) δ 7.65 (d, 2H, J=7 Hz), 7.40 (d, 2H, J=7 Hz), 2.05 (d, 3H, J=23 Hz).

Example 2

(2S)-2-fluoro-2-(4-{[(trifluoromethyl)sulfonyl] oxy}phenyl)propanoic acid (2)

To a solution of 1 (9.38 g, 29.7 mmol) in 2-propanol (150 ml), cinchonidine (8.73 g, 29.7 mmol) was added under vigorous stirring and the resulting mixture was left under reflux until to complete dissolution. After cooling at room temperature the formed precipitate was filtered off and the mother liquors were crystallized again from 2-propanol (50 mL). The collected precipitated salts (8.72 g) were dissolved in water (70 mL) and 37% HCl (2 mL) was added; the aqueous layer was extracted with $CH_2Cl_2$ (2×70 mL), dried over $Na_2SO_4$ and evaporated under vacuum to give the pure (2S)-2-fluoro-2-(4-{[(trifluoromethyl)sulfonyl]oxy}phenyl)propanoic acid (3.7 g, 11.7 mol) as pale brown solid. Yield 79%. mp 91-94° C. e.e. 96% (HPLC). $[α]_D$=+19.8 (c=0.6; $CH_3OH$). $^1$H-NMR ($CDCl_3$) δ 7.70 (d, 2H, J=7 Hz), 7.40 (d, 2H, J=7 Hz), 2.00 (d, 3H, J=23 Hz).

Example 3

(2R)-2-fluoro-2-(4-{[(trifluoromethyl)sulfonyl] oxy}phenyl)propanoic acid (3)

All the mother liquors obtained from the repeated crystallizations to afford compound 2, were collected and evaporated under vacuum to give a crude residue that was crystallized from 2-propanol (80 mL). The precipitated salt (6.60 g) was dissolved in water (50 mL) and 37% HCl (1.5 mL) was added; the aqueous layer was extracted with $CH_2Cl_2$ (2×50 mL), dried over $Na_2SO_4$ and evaporated under vacuum to give the pure (2R)-2-fluoro-2-(4-{[(trifluoromethyl)sulfonyl] oxy}phenyl)propanoic acid (3.3 g, 10.43 mol) as pale brown solid. Yield 70%. mp 90-94° C. e.e. 90% (HPLC). $[α]_D$=−20.5 (c=0.6; $CH_3OH$). $^1$H-NMR ($CDCl_3$) δ 7.70 (d, 2H, J=7 Hz), 7.40 (d, 2H, J=7 Hz), 4.80 (bs, 1H, COOH), 2.00 (d, 3H, J=23 Hz).

Example 4

4-[(1S)-1-fluoro-2-(hydroxyamino)-1-methyl-2-oxoethyl}phenyl trifluoromethanesulfonate (4)

To a solution of hydroxylamine hydrochloride (0.14 g, 2 mmol) and triethylamine (0.56 mL, 4 mmol) in dry THF (10 ml), the acid chloride derivative of 2 (1.6 mmol) was added and the reaction mixture was left stirring overnight at room temperature. After the addition of a buffer solution (pH=5.0) (10 ml) the mixture was transferred into a separator funnel, the two phases were separated and the organic one washed with water (3×10 mL), dried over $Na_2SO_4$ and evaporated under vacuum to give a crude which, after purification by flash chromatography, afforded pure 4 as a waxy solid (0.3 g, yield 56%). $[α]_D$=+15 (c=0.6; $CH_3OH$). $^1$H-NMR ($CDCl_3$) δ 9.05 (bs, 1H, CONH), 7.65 (d, 2H, J=7 Hz), 7.30 (d, 2H, J=7 Hz), 1.94 (d, 3H, J=23 Hz).

Example 5

4-[(1S)-1-fluoro-2-[hydroxyl(methyl)amino]-1-methyl-2-oxoethyl}phenyl trifluoromethane sulfonate (5)

Following the same procedure described for 4 and starting from 2 (1.6 mmol) and N-methylhydroxylamine hydrochloride (2 mmol), after workup compound 5 was isolated as a colourless oil (0.34 g, yield 63%). $[α]_D$=+10.5 (c=0.5; $CH_3OH$). $^1$H-NMR ($CDCl_3$) δ 7.65 (d, 2H, J=7 Hz), 7.30 (d, 2H, J=7 Hz), 2.90 (s, 3H), 1.94 (d, 3H, J=23 Hz).

Example 6

2-(3-benzoylphenyl)-2-fluoropropanoic acid (6)

To a cooled (T=−78° C.) solution of methyl 2-(3-benzoylphenyl)propanoate, (0.5 g, 1.85 mmol) in dry THF (5 mL), lithium hexamethyldisilazide (0.42 mL, 2.0 mmol) was added dropwise and the solution was left under stirring for 20 min; then, at −78° C., a solution of N-fluorobenzenesulfinimide (0.6 g, 1.9 mmol) in dry THF (3 ml) was added. The mixture was left stirring at room temperature overnight. After complete disappearance of the starting material (TLC) the solution was diluted with a buffer solution (pH=2.0) (10 ml) and the mixture transferred into a separator funnel. The two phases were debated and separated and the organic one was washed with water (3×10 mL), dried over $Na_2SO_4$ and evaporated under vacuum to give a crude. To a solution of the crude in dioxane (5 mL) an equal volume of NaOH 1N (5 mL) was added and the mixture was kept under stirring at room temperature overnight. After dilution with water and ice (10 mL), the mixture reaction was acidified with 1N HCl up. After exhaustive extraction of the aqueous phase with $CH_2Cl_2$ (4×20 mL), the organic extracts were combined, washed with brine (10 mL), dried over $Na_2SO_4$ and evaporated under vacuum to a crude that, after purification by flash chromatography, afforder pure 6 as colourless oil (0.27 g, yield 55%). $^1$H-NMR ($CDCl_3$) δ 8.05 (s, 1H), 7.82 (m, 4H), 7.65-7.45 (m, 4H), 2.00 (d, 3H, J=23 Hz).

Example 7

2-fluoro-2-(3-{([4-(trifluoromethyl)-1,3-thiazol-2-yl] amino}phenyl) propanoic acid (7)

To a solution of 3-nitroacetophenone (1.0 g, 6.0 mmol) in dry $CH_2Cl_2$ (10 ml), $TiCl_4$ (0.23 g, 1.21 mmol) and trimethylsilyl cyanide (0.8 mL, 6.0 mmol) were added. The mixture was left under stirring at room temperature overnight. After complete disappearance of the starting material (TLC), the solution was diluted with a buffer solution (pH=4.5) (10 ml) and the mixture transferred into a separator funnel. The two phases were debated and separated and the organic one was washed with water (3×10 mL), dried over $Na_2SO_4$ and evaporated under vacuum to give pure 2-hydroxy-2-(3-nitrophenyl) propanenitrile (1.11 g, yield 96%) as colourless oil.

To a cooled solution (T=−60° C.) of 2-hydroxy-2-(3-nitrophenyl)propanenitrile (1.11 g, 5.8 mmol) in dry $CH_2Cl_2$ (60 ml), (diethylamino)sulfur trifluoride (0.8 mL, 6.0 mmol) was added under vigorous stirring. The resulting reaction mixture was left stirring at room temperature overnight. The reaction mixture was diluted with a buffer solution (pH=5.0) (10 ml), trasferred into a separator funnel and the two phases were debated and separated. The aqueous one was extracted with water (3×10 mL); the collected organic extracts were dried over $Na_2SO_4$ and evaporated under vacuum to give a crude which was purified by flash chromatography to afford pure 2-fluoro-2-(3-nitrophenyl)propanenitrile (0.9 g, yield 79%) as brown oil. $^1$H-NMR ($CDCl_3$) δ 8.52 (s, 1H), 8.45 (d, 1H, J=3 Hz), 7.90 (m, 1H), 7.70 (t, 1H, J=7 Hz), 2.12 (d, 3H, J=23 Hz).

To a solution of 2-fluoro-2-(3-nitrophenyl)propanenitrile (0.9 g, 4.6 mmol) in $CH_3OH$ (10 ml), excess of gaseous HCl was bubbled. After complete disappearance of the starting material (TLC) the solution was diluted with water (50 ml), trasferred into a separator funnel and the two phases were debated and separated. The aqueous one was extracted with water (3×10 mL); the collected organic extracts were dried over $Na_2SO_4$ and evaporated under vacuum to give pure methyl 2-fluoro-2-(3-nitrophenyl)propanoate (1.0 g, yield 97%) as colourless oil.

Methyl 2-fluoro-2-(3-nitrophenyl)propanoate (1.0 g, 4.5 mmol) was added by portion to a suspension of Fe in a mixture of 1:5:0.05$H_2O$/MeOH/37% HCl (50 ml). The solution was refluxed for 1 hour. After cooling at room temperature, the reaction mixture was diluted with a saturated solution of $NaHCO_3$ (50 ml), trasferred into a separator funnel and extracted with EtOAc (3×100 mL), dried over $Na_2SO_4$ and evaporated under vacuum to give pure methyl 2-(3-aminophenyl)-2-fluoropropanoate as a yellow oil (0.81 g, yield 91%). $^1$H-NMR ($CDCl_3$) δ 7.15 (t, 1H, J=7 Hz), 6.85-6.75 (m, 2H), 6.75 (t, 1H, J=7 Hz), 3.80 (bs, 3H+$NH_2$), 1.95 (d, 3H, J=23 Hz).

To a solution of 2-(3-aminophenyl)-2-fluoropropanoate (0.8 g, 4.1 mmol) in toluene (6 ml), $H_2SO_4$ (0.1 mL, 2.0 mmol) was added and, after stirring for 20 min, sodium thiocyanate (0.405 g, 5.0 mmol) was added under vigorous stirring. The mixture was refluxed for 18 h. After cooling at room temperature, water (20 ml) was added and the mixture was trasferred into a separator funnel; the two phases were debated and separated and the aqueous one extracted with toluene (3×10 mL); the collected organic extracts were dried over $Na_2SO_4$ and evaporated under vacuum to give a crude that, after pulping in n-hexane, afforded pure methyl 2-{3-[(aminocarbonothioyl)amino]phenyl}-2-fluoropropanoate as orange oil (0.84 g, yield 80%).

To a solution of 2-{3-[(aminocarbonothioyl)amino]phenyl}-2-fluoropropanoate (0.84 g, 3.3 mmol) in a 1:1 dioxane/water mixture (10 mL), 3-bromo-1,1,1-trifluoroacetone (0.42 mL, 4.0 mmol) was added dropwise and the mixture refluxed for 18 h. After cooling at room temperature, a saturated solution of $NaHCO_3$ (20 mL) was added and the mixture trasferred into a separator funnel; the aqueous phase was extracted with EtOAc (3×20 mL) and the collected organic extracts dried over $Na_2SO_4$ and evaporated under vacuum to give a crude that, after purification by flash chromatography, afforded pure methyl 2-fluoro-2-(3-{[4-(trifluoromethyl)-1,3-thiazol-2-yl]amino}phenyl)propanoate as yellow solid (0.89 g, yield 77%). $^1$H-NMR ($CDCl_3$) δ 7.95 (bs, 1H, NH), 7.53 (s, 1H), 7.42 (m, 2H), 7.28 (s, 1H), 7.10 (s, 1H), 3.80 (s, 3H), 1.95 (d, 3H, J=23 Hz).

To a solution of methyl 2-fluoro-2-(3-{[4-(trifluoromethyl)-1,3-thiazol-2-yl]amino}phenyl)propanoate (0.89 g, 2.54 mmol) in 1,4-dioxane (10 ml), 37% HCl (2 mL) was added under vigorous stirring and the solution was refluxed overnight. After cooling at room temperature, 1,4-dioxane was evaporated and the resulting crude diluted with water (30 ml) and extracted with EtOAc (3×10 ml). The collected organic extracts were washed with brine (2×25 mL), dried over $Na_2SO_4$ and evaporated under vacuum to give pure 7 as a pale yellow solid (0.81 g, yield 95%). mp 140-142° C. $^1$H-NMR (DMSO-$d_6$) δ 13.60 (bs, 1H, COOH), 10.65 (bs, 1H, NH), 7.65 (m, 3H), 7.42 (t, 1H, J=7 Hz), 7.05 (d, 1H, J=7 Hz), 1.95 (d, 3H, J=23 Hz).

Example 8

4-(2-amino-1-fluoro-1-methyl-2-oxoethyl)phenyl trifluoromethanesulfonate (8)

Compound 8 was obtained as intermediate in the preparation of 1. It was isolated (89% yield) as brown solid. mp 85-87° C. $^1$H-NMR ($CDCl_3$) δ 7.75 (d, 2H, J=7 Hz), 7.30 (d, 2H, J=7 Hz), 6.42 (bs, 1H, CONH), 5.47 (bs, 1H, CONH), 1.95 (d, 3H, J=23 Hz).

Example 9

4-[(1R)-2-amino-1-fluoro-1-methyl-2-oxoethyl)phenyl trifluoromethanesulfonate (9)

Compound 3 (0.5 g, 1.6 mmol) was dissolved in thionyl chloride (5 mL) and the resulting mixture was refluxed for 3 hours. After cooling at room temperature, thionyl chloride was evaporated under vacuum and the crude acyl chloride was diluted in dry $CH_2Cl_2$ (5 mL) and cooled at T=0° C. An excess of ammonia was bubbled into the reaction solution, under vigorous stirring, until saturation of the reaction mixture. The ice-water bath was removed and the reaction mixture was left to reach room temperature. After complete disappearance of the starting material (TLC) a buffer solution (pH 2.0, V=10 ml) was added and the mixture transferred into a separator funnel; the two phases were debated and the organic one washed with water (3×10 mL), dried over $Na_2SO_4$ and evaporated under vacuum to give 9 as a white solid (0.47 g, yield 93%). mp 75-78° C. $[\alpha]_D$=+7.5 (c=0.5; $CH_3OH$). $^1H$-NMR ($CDCl_3$) δ 7.68 (d, 2H, J=7 Hz), 7.30 (d, 2H, J=7 Hz), 6.40 (bs, 1H, CONH), 5.45 (bs, 1H, CONH), 1.94 (d, 3H, J=23 Hz).

Example 10

4-[(1S)-2-amino-1-fluoro-1-methyl-2-oxoethyl)phenyl trifluoromethanesulfonate (10)

Following the same procedure described for 9 and starting from 2, after workup compound 10 was isolated as a waxy solid (0.49 g, yield 96%). $[\alpha]_D$=−7.0 (c=0.5; $CH_3OH$). $^1H$-NMR ($CDCl_3$) δ 7.75 (d, 2H, J=7 Hz), 7.28 (d, 2H, J=7 Hz), 6.45 (bs, 1H, CONH), 5.45 (bs, 1H, CONH), 1.94 (d, 3H, J=23 Hz).

Example 11

4-[1-fluoro-2-(methoxyamino)-1-methyl-2-oxoethyl] phenyl trifluoromethanesulfonate (11)

A suspension of 1 (0.5 gr, 1.6 mmol) in thionyl chloride (5 mL) was refluxed for 3 h. After cooling at room temperature, thionyl chloride was evaporated under vacuum and the crude acyl chloride was diluted in dry $CH_2Cl_2$ (5 mL) and cooled at T=0° C. by ice-water bath. Methoxyamine hydrochloride (0.27 g, 3.2 mmol) was added portionwise. The ice-water bath was removed and the reaction mixture was left stirring at room temperature. After complete disappearance of the starting material (TLC) a buffer solution (pH=2.0) (V=10 ml) was added, the two phases trasferred into a separator funnel and separated and the organic one was washed with brine (3×10 mL), dried over $Na_2SO_4$ and evaporated under vacuum to give pure 11 as pale yellow oil (0.47 gr, yield 85%). $^1H$-NMR ($CDCl_3$) δ 9.05 (bs, 1H, CONH), 7.70 (d, 2H, J=7 Hz), 7.30 (d, 2H, J=7 Hz), 3.80 (s, 3H), 1.95 (d, 3H, J=23 Hz).

Example 12

4-[1-fluoro-2-(isopropylamino)-1-methyl-2-oxoethyl]phenyl trifluoromethanesulfonate (12)

Following the same procedure described for 11 and starting from 1 and isopropylamine, after workup compound 12 was isolated as a white powder (0.5 g, yield 93%). mp 90-92° C. $^1H$-NMR ($CDCl_3$) δ 7.65 (d, 2H, J=7 Hz), 7.28 (d, 2H, J=7 Hz), 6.30 (bs, 1H, CONH), 4.10 (m, 1H), 1.94 (d, 3H, J=23 Hz), 1.27 (d, 3H, J=7 Hz), 1.15 (d, 3H, J=7 Hz).

Example 13

2-(3-benzoylphenyl)-2-fluoropropanamide (13)

Following the same procedure described for 9 and starting from 6, after workup compound 13 was isolated as a colourless oil (0.41 g, yield 93%). $^1H$-NMR ($CDCl_3$) δ 7.95 (s, 1H), 7.80-7.70 (m, 4H), 7.55 (m, 1H), 7.45-7.30 (m, 3H), 6.40 (bs, 1H, CONH), 5.45 (bs, 1H, CONH), 1.90 (d, 3H, J=23 Hz).

Example 14

2-fluoro-2-(3-{[4-(trifluoromethyl)-1,3-thiazol-2-yl] amino}phenyl)propanamide (14)

Following the same procedure described for 9 and starting from 7, after workup compound 14 was isolated as a colourless oil (0.49 g, yield 98%). $^1H$-NMR (DMSO-$d_6$) δ 10.60 (bs, 1H, NH), 7.83-7.65 (m, 3H), 7.60 (bs, 1H, CONH), 7.50 (bs, 1H, CONH), 7.40 (t, 1H, J=7 Hz), 7.15 (d, 1H, J=7 Hz), 1.78 (d, 3H, J=23 Hz).

Example 15

(2S)-2-{[(2R)-2-fluoro-2-(4-{[(trifluoromethyl)sulfonyl]oxy}phenyl)propanoyl]amino}propanoic acid (15)

Compound 3 (0.5 g, 1.6 mmol) in thionyl chloride (5 mL) was refluxed for 3 h. After cooling at room temperature, thionyl chloride was evaporated under vacuum and the crude acyl chloride was diluted in dry $CH_2Cl_2$ (5 mL), cooled at T=0° C. by ice-water bath and triethylamine (0.44 mL, 3.2 mmol) was added. L-Alanine methyl ester hydrochloride (0.22 g, 27 g, 1.6 mmol) was added portionwise, the ice-water bath removed and the reaction mixture was left stirring at room temperature. After complete disappearance of the starting material (TLC) a buffer solution (pH=2.0) (V=10 ml) was added, the two phases trasferred into a separator funnel and separated. The organic layer was washed with brine (3×10 mL), dried over $Na_2SO_4$ and evaporated under vacuum to give 2-[2-(4-trifluoromethanesulfonyloxyphenyl)propionylamino]propionic acid methyl ester as pale yellow oil (0.44 gr, yield 72%).

To a solution of the methyl ester (0.44 g, 1.15 mmol) in dry THF (5 ml), 1N NaOH (1.4 ml) was added and the reaction mixture was left under stirring at room temperature overnight. The reaction mixture was quenched by the addition of a buffer solution (pH=2.0) (V=10 ml), transferred into a separator funnel and extracted with $CH_2Cl_2$ (3×10 mL); the collected organic extracts were dried over $Na_2SO_4$ and evaporated under vacuum to give pure 15 (0.38 g, yield 90%), as colourless oil. $^1H$-NMR (DMSO-$d_6$) δ 12.70 (bs, 1H, COOH), 8.45 (bs, 1H, CONH), 7.72 (d, 2H, J=7 Hz), 7.40 (d, 2H, J=7 Hz), 4.28 (m, 1H), 1.85 (d, 3H, J=23 Hz), 1.30-1.15 (m, 3H).

Example 16

(2S)-2-{[2-fluoro-2-(3-{[4-(trifluoromethyl)-1,3-thiazol-2-yl]amino}phenyl)propanoyl] amino}propanoic acid (16)

Following the same procedure described for 15 and starting from 7, after workup compound 16 was isolated as a pale yellow oil (0.41 g, yield 60% from 7). $^1H$-NMR (DMSO-$d_6$) δ 12.70 (bs, 1H, COOH), 10.65 (bs, 1H, NH), 8.45 (bs, 1H, CONH), 7.75-7.60 (m, 3H), 7.45 (m, 1H), 7.18 (m, 1H), 4.28 (m, 1H), 1.85 (d, 3H, J=23 Hz), 1.30-1.15 (m, 3H).

Example 17

4-{(1R)-1-fluoro-1-methyl-2-[(methylsulfonyl)amino]-2-oxoethyl}phenyl trifluoromethanesulfonate (17)

To a solution of 3 (0.5 g, 1.6 mmol) in dry $CH_2Cl_2$ (10 ml), N,N-carbonyldiimidazole (0.33 g, 2.0 mmol) was added under vigorous stirring. After 1 h methanesulfonamide (0.19 g, 2 mmol) and triethylamine (0.28 mL, 2 mmol) were added and the resulting mixture was left stirring overnight at room temperature. The organic mixture was washed with a saturated solution of $NaHCO_3$ (2×10 mL) and brine (3×10 mL), dried over $Na_2SO_4$ and evaporated under vacuum to give pure 17 as a colourless oil (0.60 g, yield 95%). $[\alpha]_D = +9$ (c=1; $CH_3OH$). $^1$H-NMR (DMSO-$d_6$) δ 7.70 (d, 2H, J=7 Hz), 7.55 (d, 2H, J=7 Hz), 3.05 (s, 3H), 1.85 (d, 3H, J=23 Hz).

Example 18

4-{(1S)-1-fluoro-1-methyl-2-oxo-2-(2-pyrrolidin-1-ylethyl)amino]ethyl}phenyl trifluoromethanesulfonate (18)

Following the same procedure described for 11 and starting from 2 and 3-pyrrolidin-1-ylpropan-1-amine (prepared as previously described), after workup compound 18 was isolated as a colourless oil (0.42 g, yield 62%). $[\alpha]_D = -14$ (c=0.5; $CH_3OH$). $^1$H-NMR ($CDCl_3$) δ 7.90 (bs, 1H, CONH), 7.80 (d, 2H, J=7 Hz), 7.30 (d, 2H, J=7 Hz), 3.75 (m, 1H), 3.62 (m, 1H), 3.55-3.30 (m, 2H), 3.00-2.82 (m, 2H), 2.75-2.54 (m, 2H), 2.30-2.05 (m, 6H), 1.95 (d, 3H, J=23 Hz).

Example 19

4-((1R)-1-fluoro-1-methyl-2-oxo-2-{[(2R)-pyrrolidin-2-ylmethyl]amino}ethyl)phenyl trifluoromethanesulfonate (19)

Following the same procedure described for 12 and starting from 3 and 1-[(2R)-pyrrolidin-2-yl]methanamine, after workup compound 19 was isolated as a colourless oil (0.44 g, yield 69%). $[\alpha]_D = +17$ (c=0.3; $CH_3OH$). $^1$H-NMR ($CDCl_3$) δ 7.75 (d, 2H, J=7 Hz), 7.40 (bs, 1H, CONH), 7.20 (d, 2H, J=7 Hz), 3.52-3.35 (m, 2H), 3.30 (m, 1H), 3.10-2.90 (m, 2H), 1.95 (d, 3H, J=23 Hz), 1.85-1.70 (m, 4H).

The invention claimed is:

1. A compound of formula (I) or single enantiomers or pharmaceutically acceptable salts thereof,

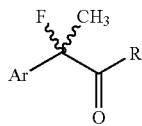

wherein
Ar is a phenyl group substituted by one or more groups independently selected from F, Br, I, $C_2$-$C_4$-alkenyl, $C_2$-$C_4$-alkynyl, hydroxy, $C_1$-$C_4$-acyloxy, cyano, heteroarylamino, $C_1$-$C_4$-acylamino, halo-$C_1$-$C_3$-alkyl, halo-$C_1$-$C_3$-alkoxy, benzoyl, heteroarylcarbonyl, heteroaryl, linear or branched $C_1$-$C_8$-alkanesulfonate, linear or branched $C_1$-$C_8$-alkanesulfonamides, linear or branched $C_1$-$C_8$-alkyl sulfonylmethyl; or Ar is a heteroaryl ring selected from pyrrole, thiofene, furane, indole;
R is OH or a residue of formula NR'R''
wherein
R' group is selected from
H, OH and
when R' is H, R'' is selected from
H, $C_1$-$C_5$-alkyl, $C_3$-$C_6$-cycloalkyl, $C_2$-$C_5$-alkenyl, $C_1$-$C_5$-alkoxy;
an heteroaryl group selected from substituted and unsubstituted pyridine, pyrimidine, pyrrole, thiofene, furane, indole, thiazole, oxazole;
an amino acid residue comprising straight or branched $C_1$-$C_6$-alkyl, $C_3$-$C_6$-cycloalkyl, $C_2$-$C_6$-alkenyl, $C_1$-$C_6$-phenylalkyl, substituted with one further carboxy (COOH) group;
a residue of formula —$CH_2$—$CH_2$—Z—($CH_2$—$CH_2$O$)_n$R* wherein R* is H or $C_1$-$C_5$-alkyl, n is an integer from 0 to 2 and Z is oxygen or sulfur;
a residue of formula —($CH_2)_n$—$NR_aR_b$ wherein n is an integer from 0 to 5 and each $R_a$ and $R_b$, which may be the same or different, are $C_1$-$C_6$-alkyl, $C_2$-$C_6$-alkenyl or, alternatively, $R_a$ and $R_b$, together with the nitrogen atom to which they are bound, form a heterocycle from 3 to 7 members of formula (II)

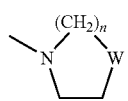

wherein W represents a single bond, O, S, N—$R_c$, $R_c$ being H, $C_1$-$C_6$-alkyl or $C_1$-$C_6$-alkylphenyl, and n is an integer from 0 to 3,
a residue of formula $SO_2R_d$ wherein $R_d$ is $C_1$-$C_6$-alkyl, $C_3$-$C_6$-cycloalkyl, $C_2$-$C_6$-alkenyl, aryl and heteroaryl;
when R' is OH, R'' is selected from H, $C_1$-$C_6$-alkyl, $C_3$-$C_6$-cycloalkyl, $C_2$-$C_5$-alkenyl with the proviso that compounds of the general formula (I) exclude 2-(3-benzoylphenyl)-2-fluoropropanoic acid.

2. A compound according to claim 1 wherein:
Ar is a phenyl group substituted by one or more groups independently selected from: benzoyl, 4-trifluoromethyl-2-amino-thiazole, 4-trifluoromethyl-2-amino-oxazole, trifluoromethanesulfonyloxy, trifluoromethanesulfonylamino, benzylsulfonyloxy, benzenesulfonyloxy, 2'-chlorobenzenesulfonyloxy, methanesulfonylamino, 2-propanesulfonylamino, benzylsulfonylamino, benzenesulfonylamino, 2'-ethylbenzenesulfonylamino, aminosulfonylmethyl, 2'-chlorobenzenesulfonylamino, benzenesulfonylmethyl, aminosulfonyloxy, aminosulfonylamino;
R is OH or a residue of formula NR'R''
wherein
when R' is H, R'' is selected from
H, $C_1$-$C_5$ alkyl, $C_3$-$C_6$ cycloalkyl, $C_1$-$C_5$ alkoxy, $C_1$-$C_2$-carboxyalkyl;
an heteroaryl group selected from substituted and unsubstituted pyridine, thiazole, oxazole; a residue of formula —($CH_2)_n$—$NR_aR_b$ wherein n is the integer 2 or 3, more preferably 3 and the group $NR_aR_b$ is N,N-dimethylamine, N,N-diethylamine, 1-piperidyl, 1-pirrolidinyl, 4-morpholyl, 1-pyrrolidyl, 1-piperazinyl, 1-(4-methyl)piperazinyl;

a residue of formula $SO_2R_d$ wherein $R_d$ is $C_1$-$C_2$-alkyl, $C_3$-$C_6$ cycloalkyl when R' is OH, R" is H, $C_1$-$C_5$ alkyl, $C_3$-$C_6$ cycloalkyl.

3. A compound according to claim 1 selected from:
2-fluoro-2-(4-{[(trifluoromethyl)sulfonyl]oxy}phenyl)propanoic acid;
(2S)-2-fluoro-2-(4-{[(trifluoromethyl)sulfonyl]oxy}phenyl)propanoic acid;
(2R)-2-fluoro-2-(4-{[(trifluoromethyl)sulfonyl]oxy}phenyl)propanoic acid;
4-[(1S)-1-fluoro-2-(hydroxyamino)-1-methyl-2-oxoethyl}phenyl trifluoromethanesulfonate;
4-[(1S)-1-fluoro-2-[hydroxyl(methyl)amino]-1-methyl-2-oxoethyl}phenyl trifluoromethanesulfonate;
2-fluoro-2-(3-{[4-(trifluoromethyl)-1,3-thiazol-2-yl]amino}phenyl)propanoic acid;
4-(2-amino-1-fluoro-1-methyl-2-oxoethyl)phenyl trifluoromethanesulfonate;
4-[(1R)-2-amino-1-fluoro-1-methyl-2-oxoethyl)phenyl trifluoromethanesulfonate;
4-[(1S)-2-amino-1-fluoro~1-methyl-2-oxoethyl)phenyl trifluoromethanesulfonate;
4-[1-fluoro-2-(methoxyamino)-1-methyl-2-oxoethyl]phenyl trifluoromethanesulfonate;
4-[1-fluoro-2-(isopropylamino)-1-methyl-2-oxoethyl]phenyl trifluoromethanesulfonate;
2-(3-benzoylphenyl)-2-fluoropropanamide;
2-fluoro-2-(3-{[4-(trifluoromethyl)-1,3-thiazol-2-yl]amino}phenyl)propanamide;
(2S)-2-{[(2R)-2-fluoro-2-(3-{[4-(trifluoromethyl)-1)-3-thiazol-2-yl]amino}phenyl)propanoyl]amino}propanoic acid;
(2S)-2-{[2-fluoro-2-(3-{[4-(trifluoromethyl)-1,3-thiazol-2-yl]amino}phenyl)propanoyl]amino}propanoic acid;
4-{(1R)-1-fluoro-1-methyl-2-[(methylsulfonyl)amino]-2-oxoethyl}phenyl trifluoromethanesulfonate;
4-{(1S)-1-fluoro-1-methyl-2-oxo-2-(2-pyrrolidin-1-yl-ethyl)amino]ethyl}phenyl trifluoromethanesulfonate; and
4-((1R)-1-fluoro-1-methyl-2-oxo-2-{[(2R)-pyrrolidin-2-ylmethyl]amino}ethyl)phenyl trifluoromethanesulfonate.

4. A pharmaceutical composition comprising a therapeutically effective amount of a compound of formula (I) or single enantiomers or pharmaceutically acceptable salts thereof,

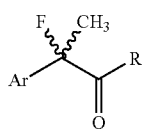

(I)

wherein

Ar is a phenyl group unsubstituted or substituted by one or more groups independently selected from halogen, $C_2$-$C_4$-alkenyl, $C_2$-$C_4$-alkynyl, $C_1$-$C_4$-alkoxy, hydroxy, $C_1$-$C_4$-acyloxy, cyano, nitro, heteroarylamino, $C_1$-$C_4$-acylamino, halo-$C_1$-$C_3$-alkyl, halo-$C_1$-$C_3$-alkoxy, benzoyl, heteroarylcarbonyl, heteroaryl, linear or branched $C_1$-$C_8$-alkanesulfonate, linear or branched $C_1$-$C_8$-alkanesulfonamides, linear or branched $C_1$-$C_8$-alkyl sulfonylmethyl; or Ar is a heteroaryl ring selected from pyridine, pyrrole, thiofene, furane, indole;

R is OH or a residue of formula NR'R"

wherein

R' group is selected from

H, OH and when R' is H, R" is selected from

H, $C_1$-$C_5$-alkyl, $C_3$-$C_6$-cycloalkyl, $C_2$-$C_5$-alkenyl, $C_1$-$C_5$-alkoxy;

an heteroaryl group selected from substituted and unsubstituted pyridine, pyrimidine, pyrrole, thiofene, furane, indole, thiazole, oxazole;

an amino acid residue comprising straight or branched $C_1$-$C_6$-alkyl, $C_3$-$C_6$-cycloalkyl, $C_2$-$C_6$-alkenyl, $C_1$-$C_6$-phenylalkyl, substituted with one further carboxy (COOH) group;

a residue of formula —$CH_2$—$CH_2$—Z—($CH_2$—$CH_2O)_nR^*$ wherein $R^*$ is H or $C_1$-$C_5$-alkyl, n is an integer from 0 to 2 and Z is oxygen or sulfur;

a residue of formula —$(CH_2)_n$—$NR_aR_b$ wherein n is an integer from 0 to 5 and each $R_a$ and $R_b$, which may be the same or different, are $C_1$-$C_6$-alkyl, $C_2$-$C_6$-alkenyl or, alternatively, $R_a$ and $R_b$, together with the nitrogen atom to which they are bound, form a heterocycle from 3 to 7 members of formula (II)

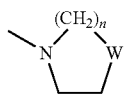

(II)

wherein W represents a single bond, O, S, N—$R_c$, $R_c$ being H, $C_1$-$C_6$-alkyl or $C_1$-$C_6$-alkylphenyl, and n is an integer from 0 to 3, a residue of formula $SO_2R_d$ wherein $R_d$ is $C_1$-$C_6$-alkyl, $C_3$-$C_6$-cycloalkyl, $C_2$-$C_6$-alkenyl, aryl and heteroaryl;

when R' is OH, R" is selected from H, $C_1$-$C_6$-alkyl, $C_3$-$C_6$-cycloalkyl, $C_2$-$C_5$-alkenyl; with the proviso that compounds of the general formula (I) exclude 2-(3-benzoylphenyl)-2-fluoropropanoic acid;

in admixture with a suitable carrier thereof.

5. A method for the treatment of a disease which responds to the inhibition of the CXCL8- and C5a-induced chemotaxis of polymorphonucleate and mononucleate cells, said method comprising administering to a subject in need thereof a therapeutically effective amount of a compound of formula (I) or single enantiomers or pharmaceutically acceptable salts thereof,

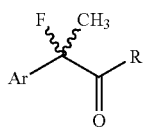

(I)

wherein

Ar is a phenyl group unsubstituted or substituted by one or more groups independently selected from halogen, $C_1$-$C_4$-alkyl, $C_2$-$C_4$-alkenyl, $C_2$-$C_4$-alkynyl, $C_1$-$C_4$-alkoxy, hydroxy, $C_1$-$C_4$-acyloxy, phenoxy, cyano, nitro, amino, $C_1$-$C_4$-acylamino, halo-$C_1$-$C_3$-alkyl, halo-$C_1$-

$C_3$-alkoxy, benzoyl, heteroarylcarbonyl, heteroaryl, linear or branched $C_1$-$C_8$-alkanesulfonate, linear or branched $C_1$-$C_8$-alkanesulfonamides, linear or branched $C_1$-$C_8$-alkyl sulfonylmethyl; or Ar is a heteroaryl ring selected from pyridine, pyrrole, thiofene, furane, indole;

R is OH or a residue of formula NR'R"
wherein
R' group is selected from
  H, OH and
  when R' is H, R" is selected from
    H, $C_1$-$C_5$-alkyl, $C_3$-$C_6$-cycloalkyl, $C_2$-$C_5$-alkenyl, $C_1$-$C_5$-alkoxy;
    an heteroaryl group selected from substituted and unsubstituted pyridine, pyrimidine, pyrrole, thiofene, furane, indole, thiazole, oxazole;
    an amino acid residue comprising straight or branched $C_1$-$C_6$-alkyl, $C_3$-$C_6$-cycloalkyl, $C_2$-$C_6$-alkenyl, $C_1$-C6-phenylalkyl, substituted with one further carboxy (COOH) group;
    a residue of formula —$CH_2$—$CH_2$—Z—($CH_2$—$CH_2O)_nR^*$ wherein $R^*$ is H or $C_1$-$C_5$-alkyl, n is an integer from 0 to 2 and Z is oxygen or sulfur;
    a residue of formula —$(CH_2)_n$—$NR_aR_b$ wherein n is an integer from 0 to 5 and each $R_a$ and $R_b$, which may be the same or different, are $C_1$-$C_6$-alkyl, $C_2$-$C_6$-alkenyl or, alternatively, $R_a$ and $R_b$, together with the nitrogen atom to which they are bound, form a heterocycle from 3 to 7 members of formula (II)

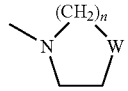

(II)

wherein W represents a single bond, O, S, N—$R_c$, $R_c$ being H, $C_1$-$C_6$-alkyl or $C_1$-$C_6$-alkylphenyl, and n is an integer from 0 to 3,
    a residue of formula $SO_2R_d$ wherein $R_d$ is $C_1$-$C_6$-alkyl, $C_3$-$C_6$-cycloalkyl, $C_2$-$C_6$-alkenyl, aryl and heteroaryl;
  when R' is OH, R" is selected from H, $C_1$-$C_6$-alkyl, $C_3$-$C_6$-cycloalkyl, $C_2$-$C_5$-alkenyl, wherein the disease is selected from the group consisting of sepsis, psoriasis, bullous pemphigoid, rheumatoid arthritis, ulcerative colitis, acute respiratory distress syndrome, idiopathic fibrosis, cystic fibrosis, chronic obstructive pulmonary disease, glomerulonephritis and in the treatment of injury caused by ischemia and reperfusion.

6. The method according to claim 5, wherein the compound of formula (I) is 2-(3-benzoylphenyl)-2-fluoropropanoic acid.

* * * * *